United States Patent
Depierro et al.

(10) Patent No.: US 10,246,473 B2
(45) Date of Patent: Apr. 2, 2019

(54) PROCESS FOR PREPARING AN ACRYLOYLOXYSILANE

(71) Applicant: Dow Corning Corporation, Midland, MI (US)

(72) Inventors: Michael A. Depierro, Midland, MI (US); Sean P Reisch, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/567,391

(22) PCT Filed: Jun. 17, 2016

(86) PCT No.: PCT/US2016/038075
§ 371 (c)(1),
(2) Date: Oct. 18, 2017

(87) PCT Pub. No.: WO2016/205648
PCT Pub. Date: Dec. 22, 2016

(65) Prior Publication Data
US 2018/0134734 A1    May 17, 2018

Related U.S. Application Data

(60) Provisional application No. 62/182,169, filed on Jun. 19, 2015.

(51) Int. Cl.
*C07F 7/20* (2006.01)
*C07F 7/18* (2006.01)

(52) U.S. Cl.
CPC .............. *C07F 7/20* (2013.01); *C07F 7/1804* (2013.01)

(58) Field of Classification Search
None
See application file for complete search history.

(56) References Cited

U.S. PATENT DOCUMENTS

| | | |
|---|---|---|
| 8,476,375 B2 | 6/2013 | Backer et al. |
| 8,580,886 B2 | 11/2013 | Backer et al. |
| 8,692,012 B2 | 4/2014 | Daiss et al. |
| 9,249,164 B2 | 2/2016 | Hupfield et al. |
| 9,452,575 B2 | 9/2016 | Urushidani et al. |
| 9,518,072 B2 | 12/2016 | Backer et al. |
| 2012/0283362 A1 | 11/2012 | Backer et al. |
| 2013/0060057 A1* | 3/2013 | Daiss .................... C07F 7/1892 556/440 |
| 2013/0184482 A1 | 7/2013 | Hupfield et al. |
| 2014/0011900 A1 | 1/2014 | Burns et al. |
| 2014/0031487 A1 | 1/2014 | Guy et al. |
| 2015/0126676 A1* | 5/2015 | Backer ..................... B60C 1/00 524/570 |

FOREIGN PATENT DOCUMENTS

| | | |
|---|---|---|
| WO | 2012050761 | 4/2012 |
| WO | 2016205642 | 12/2016 |

OTHER PUBLICATIONS

Hydrotreated Petroleum Distillates; https://chem.nlm.nih.gov/chemidplus/rn/64742-55-8 Sep. 5, 2018 (Year: 2018).*
Hydroseal—Source & Details; Handbook of Green Chemicals, 2004, p. 270 and; Total (approved 2002). (Year: 2002).*
Osterholtz FD, et al. "Kinetics of the hydrolysis and condensation of organofunctional alkoxysilances: a review", Journal of Adhesion Science and Technology, Taylor & Francis, GB, vol. 6, No. 1, 1992, pp. 127-149, XP008098738.
Search Report from corresponding Japanese application 2017-565282, dated Dec. 3, 2018.

* cited by examiner

*Primary Examiner* — Clinton A Brooks
*Assistant Examiner* — Kofi Adzamli
(74) *Attorney, Agent, or Firm* — Catherine U. Brown

(57) ABSTRACT

A process for purifying an acryloyloxysilane comprising subjecting a mixture comprising an acryloyloxysilane, a haloorganoalkoxysilane, and an alkane-based non-polar solvent to a temperature and pressure sufficient to vaporize a portion of the non-polar solvent, the haloorganoalkoxysilane, or the non-polar solvent and the haloorganoalkoxysilane from the mixture to produce a purified mixture comprising the acryloyloxysilane. The examples disclose a three-step short-path distillation process, where in the first two passes, the residue-fraction is the one containing the product, whereas in the third path, the distillate is containing the purified product.

19 Claims, 3 Drawing Sheets

US 10,246,473 B2

PROCESS FOR PREPARING AN ACRYLOYLOXYSILANE

CROSS-REFERENCE TO RELATED APPLICATIONS

This application is a U.S. national stage filing under 35 U.S.C. § 371 of PCT Application No. PCT/US16/038075 filed 17 Jun. 2016, currently pending, which claims the benefit of U.S. Provisional Patent Application No. 62/182169 filed 19 Jun. 2015 under 35 U.S.C. § 119 (e). PCT Application No. PCT/US16/038075 and U.S. Provisional Patent Application No. 62/182169 are hereby incorporated by reference.

FIELD OF THE INVENTION

The present invention relates to a process for preparing a purified acryloyloxysilane. More specifically, the present invention relates to a process for subjecting a mixture comprising an acryloyloxysilane, a haloorganoalkoxysilane, and a non-polar solvent, to a temperature and pressure to vaporize a portion of the non-polar solvent, the haloorganoalkoxysilane, or the non-polar solvent and the haloorganoalkoxysilane from the mixture to produce a purified mixture comprising the acryloyloxysilane.

BACKGROUND OF THE INVENTION

Unsaturated organoalkoxysilanes containing an acryloyloxy group, such as 3-acryloyloxypropyltriethoxysilane, have been produced by the nucleophilic substitution reaction of a haloorganoalkoxysilane with a metal salt of an unsaturated carboxylic acid, such as sodium acrylate, in the presence of a suitable phase-transfer catalyst. In addition to the desired silane product, this process produces a crude mixture comprising the acryloyloxysilane, a metal halide precipitate, and unreacted reactants. The metal halide precipitate is removed by filtration or washing with brine or water.

Although there are methods of removing the unreacted starting materials, solvents, and unwanted reaction products, these methods have not been adequate to produce acryloyloxysilanes with the low levels of impurities, such as unreacted starting materials, demanded by many of the applications where acryloyloxysilanes are used today. One of the issues with the present methods is that the starting material and the acryloyloxysilanes may vaporize at similar temperatures making separation by distillation difficult. Furthermore, repeated distillation steps required to separate the starting materials sometimes cause the formation of dimers and other oligomers of the target acryloyloxysilane product reducing yields and further increasing impurity issues.

Therefore, there is a need for processes for purifying acryloyloxysilanes that quickly separate unreacted starting materials, solvents, and undesired reaction products from the desired acryloyloxysilane without reducing yields through the formation of dimers and other oligomers of the acryloyloxysilane.

BRIEF SUMMARY OF THE INVENTION

The present invention is directed to a process for purifying an acryloyloxysilane comprising subjecting a mixture comprising an acryloyloxysilane, a haloorganoalkoxysilane, and a non-polar solvent, wherein the non-polar solvent comprises a branched-chain alkane having from 5 to 20 carbon atoms or a mixture of a branched-chain alkane having from 5 to 20 carbon atoms and a straight-chain alkane having from 5 to 14 carbon atoms, and wherein the non-polar solvent comprises less than 5% (w/w), based on the weight of the non-polar solvent, of an aromatic compound, to a temperature and pressure sufficient to vaporize a portion of the non-polar solvent, the haloorganoalkoxysilane, or the non-polar solvent and the haloorganoalkoxysilane from the mixture to produce a purified mixture comprising the acryloyloxysilane.

The processes of the present invention produces a purified acryloyloxysilane which may be used as a coupling agent for unsaturated resin or polymer systems, an adhesion promoter at organic-inorganic interfaces, and as a surface modifier.

DETAILED DESCRIPTION OF THE INVENTION

Figure 1:
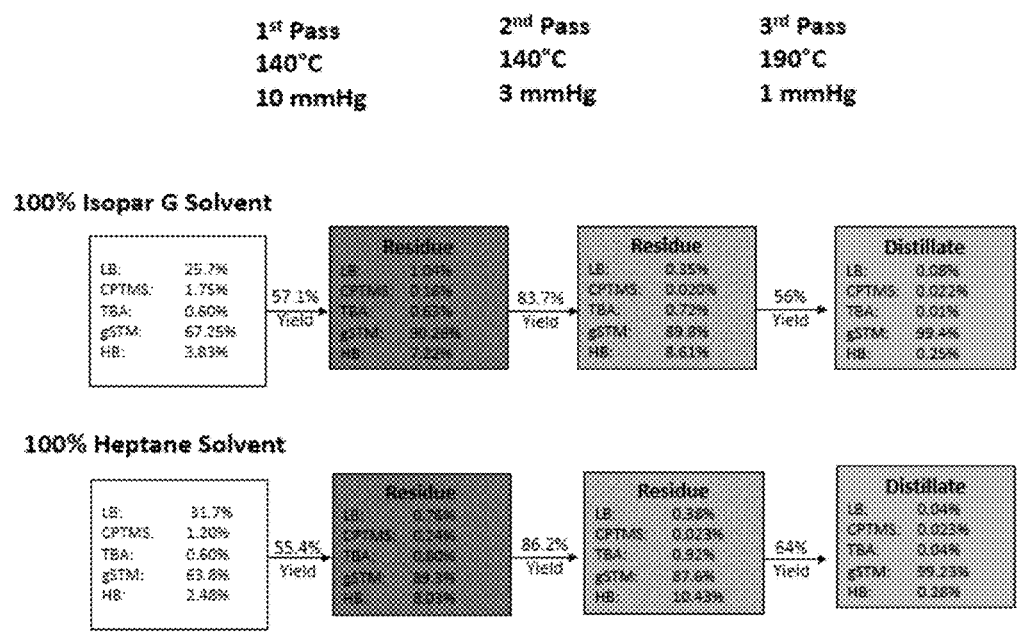
FIG. 1 is a diagram of the process in EXAMPLE 1.

A process for purifying an acryloyloxysilane, the process comprising: subjecting a mixture comprising an acryloyloxysilane, a haloorganoalkoxysilane, and a non-polar solvent, wherein the non-polar solvent comprises a branched-chain alkane having from 5 to 20 carbon atoms or a mixture of a branched-chain alkane having from 5 to 20 carbon atoms and a straight-chain alkane having from 5 to 14 carbon atoms, and wherein the non-polar solvent comprises less than 5% (w/w), based on the weight of the non-polar solvent, of an aromatic compound, to a temperature and pressure sufficient to vaporize a portion of the non-polar solvent, the haloorganoalkoxysilane, or the non-polar solvent and the haloorganoalkoxysilane from the mixture to produce a purified mixture comprising the acryloyloxysilane.

The mixture comprises an acryloyloxysilane, a haloorganoalkoxysilane, and a non-polar solvent. As used herein, "acryloyloxysilane" is intended to include materials that include the acryloyloxy functionality. For example, it is contemplated that acryloyloxy may include sorbyloxy functional groups.

In one embodiment, the acryloyloxysilane has the formula $CR^6_2=CR^1COOR^3Si(OR^4)_nR^5_{3-n}$ (IV), wherein $R^1$ is H, $R^7COO^-M^{a+}$, or $C_1$-$C_6$ hydrocarbyl, $R^3$ is $C_1$-$C_6$ hydrocarbylene, each $R^4$ is independently $C_1$-$C_{10}$ hydrocarbyl, each $R^5$ is independently H, $R^7COO^-M^{a+}$, or $C_1$-$C_6$ hydrocarbyl, each $R^6$ is independently H, $C_1$-$C_6$ hydrocarbyl, or $COOR^3Si(OR^4)_nR^5_{3-n}$, $R^7$ is hydrocarbylene having from 1 to 6 carbon atoms, n is an integer from 1 to 3, $M^{a+}$ is an alkali metal cation or alkaline earth metal cation, a is the cationic charge and has a value of 1 or 2.

Examples of the acryloyloxysilane include, but are not limited to, sorbyloxymethyldimethylmethoxysilane, γ-sorbyloxypropylmethydimethoxysilane, γ-sorbyloxypropyltrimethoxysilane, γ-sorbyloxypropyltriethoxysilane, γ-sorbyloxybutyldimethoxysilane, methacryloyloxymethyldimethylmethoxysilane, γ-methacryloyloxypropylmethydimethoxysilane, γ-methacryloyloxypropyltrimethoxysilane, γ-methacryloyloxypropyltriethoxysilane, γ-methacryloyloxybutyldimethoxysilane, δ-methacryloyloxybutyltrimethoxysilane, δ-methacryloyloxybutylmethyldimethoxysilane, acryloyloxymethyldimethylmethoxysilane, γ-acryloyloxypropylmethyldimethoxysilane, γ-acryloyloxypropyltrimethoxysilane, γ-acryloyloxypropyltriethoxysilane, γ-acryloyloxypropylbutyldimethoxysilane, δ-acryloyloxybutyltrimethoxysilane, δ-acryloyloxybutylmethyldimethoxysilane, bis(γ-trimethoxysilylpropyl) fumarate, bis(γ-triethoxysilylpropyl) fumarate, bis(γ-trimethoxysilylpropyl) maleate, bis(γtriethoxysilylpropyl) maleate, bis(γ-trimethoxysilylpropyl) itaconate, bis(γ-triethoxysilylpropyl) itaconate.

The acryloyloxysilane may be prepared by methods known in the art. In one embodiment, the acryloyloxysilane is prepared by reacting a metal salt of a carboxylic acid having the formula $[CR^2_2=CR^1COO^-]_aM^{a+}$ (I), with a haloorganoalkoxysilane having the formula $XR^3Si(OR^4)_nR^5_{3-n}$ (II) at a temperature of from 50 to 160 °C. and in the presence of a catalyst, and in the presence of water, an alcohol comprising 1 to 5 carbon atoms, or a combination of water and an alcohol comprising 1 to 5 carbon atoms, to form a mixture comprising an acryloyloxysilane and a metal halide having the formula $M^{a+}X^-_a$ (III), wherein $R^1$ is H, $R^7COO^-$ $M^{a+}$, or $C_1$-$C_6$ hydrocarbyl, each $R^2$ is independently $R^1$ or $[COO^-]M^{a+}$, $M^{a+}$ is an alkaline metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

The metal salt of an unsaturated carboxylic acid has the formula $[CR^2_2=CR^1COO^-]_aM^{a+}$ (I). Examples of alkali metal or alkaline earth metal cations represented by $M^{a+}$ include, but are not limited to, $Li^+$, $Na^+$, $K^+$, $Mg^{2+}$, and $Ca^{2+}$. In one embodiment, $M^{a+}$ is $Na^+$ or $K^+$.

The hydrocarbyl groups represented by $R^1$ and $R^2$ typically have from 1 to 6 carbon atoms, alternatively from 1 to 4 carbon atoms, alternatively from 1 to 3 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. In one embodiment, one $R^2$ group is hydrogen and one $R^2$ group is propenyl (i.e., $CH_3CHCH-$).

Examples of the metal salt of an unsaturated carboxylic acid include, but are not limited to, sodium acrylate, sodium methacrylate, sodium ethacrylate (i.e., sodium 2-methylenebutanoate), sodium crotonate, sodium isocrotonate, sodium sorbate, potassium acrylate, potassium methacrylate, potassium ethacrylate (i.e., potassium 2-methylenebutanoate), potassium crotonate, potassium isocrotonate, potassium sorbate, magnesium acrylate, magnesium methacrylate, magnesium ethacrylate, magnesium crotonate, magnesium isocrotonate, magnesium sorbate, calcium acrylate, calcium methacrylate, calcium ethacrylate, calcium crotonate, calcium isocrotonate, and calcium sorbate, monosodium fumarate, disodium fumarate, monosodium maleate, disodium maleate, monosodium itaconate, disodium itaconate, monopotassium fumarate, dipotassium fumarate, monopotassium maleate, dipotassium maleate, monopotassium itaconate, dipotassium itaconate.

Processes of preparing metal salts of unsaturated carboxylic acids are well known in the art, and many of these compounds are commercially available. For example, the metal salt of an unsaturated carboxylic acid may be prepared by adding an unsaturated carboxylic acid dropwise to a solution of NaOEt in ethanol while maintaining the temperature below 25° C. and then stirring for one hour.

The haloorganoalkoxysilane has the formula $XR^3Si(OR^4)_nR^5_{3-n}$ (II), where X is halo. Examples of halo atoms represented by X include —F, —Cl, —Br, and —I.

The hydrocarbylene groups represented by $R^3$ typically have from 1 to 6 carbon atoms, alternatively from 2 to 4 carbon atoms, alternatively 3 carbon atoms. Hydrocarbylene groups containing at least three carbon atoms can have a branched or unbranched structure. Examples of hydrocarbylene groups include, but are not limited to, methylene, ethylene, propylene, 1-methylethylene, butylene, 1-methylpropylene, 2-methylpropylene, 1,1-dimethylethylene, pentylene, 1-methylbutylene, 1-ethylpropylene, 2-methylbutylene, 3-methylbutylene, 1,2-dimethylpropylene, 2,2-dimethylpropylene, hexylene, or a similar hydrocarbylene group.

The hydrocarbyl groups represented by $R^4$ typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$ above and alkyl, such as hexyl, heptyl, octyl, nonyl, and decyl; cycloalkyl, such as methylcyclohexyl; aryl, such as napthyl; alkaryl such as tolyl and xylyl; aralkyl, such as benzyl and phenylethyl; and aralkenyl, such as styryl and cinnamyl.

The hydrocarbyl groups represented by $R^5$ typically have from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$.

Examples of the haloorganoalkoxysilane of formula (II) include, but are not limited to, chloromethyldimethylmethoxysilane, chloromethyltrimethoxysilane, chloromethyltriethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, 3-chloropropylethyldimethoxysilane, 3-chloropropylethyldiethoxysilane, 3-bromopropyltrimethoxysilane, 3-bromopropyltriethoxysilane, 3-iodopropyltrimethoxysilane, 3-iodopropyltriethoxysilane. In one embodiment, the haloorganoalkoxysilane of formula (II) is 3-chloropropyltrimethoxy silane or 3-chloropropyltriethoxysilane.

Processes of preparing haloorganoalkoxysilanes are well known in the art; many of these compounds are commercially available.

The process to prepare the acryloyloxysilane may be conducted by reacting the starting materials used in the reaction in the presence of water, an alcohol comprising 1 to 5 carbon atoms, or a combination of water and an alcohol comprising 1 to 5 carbon atoms. The water may be deionized or distilled water or may be water present in other reactants.

In one embodiment, the reacting to form the acryloyloxysilane is in the presence of an alcohol comprising from 1 to 5 carbon atoms, alternatively from 1 to 3 carbon atoms, alternatively 1 carbon atom. In one embodiment, the alcohol is according to the formula $R^7OH$, where $R^7$ is hydrocarbyl group comprising from 1 to 5 carbon atoms. Acyclic hydrocarbyl $R^7$ groups containing at least three carbon atoms can have a branched or unbranched structure.

Examples of hydrocarbyl groups represented by $R^7$ include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl.

The alcohol having from 1 to 5 carbon atoms may be a primary, secondary, or tertiary alcohol when possible; alternatively primary or secondary, alternatively primary. Examples of the alcohol having from 1 to 5 carbon atoms include, but are not limited to, methanol, ethanol, propanol, isopropanol, butanol, isobutanol, sec-butanol, pentanol, and isopentanol. In one embodiment, the alcohol is methanol. Alcohols suitable for the present invention are available commercially.

The catalyst used to make the acryloyloxysilane is any catalyst known to function as a catalyst in the reaction between a metal salt of an unsaturated carboxylic acid and a haloorganoalkoxysilane to form an acryloyloxysilane, alternatively, the catalyst is a phase-transfer catalyst, wherein the phase transfer catalyst is any phase-transfer catalyst known to function as a solid-solution phase-transfer catalyst in the nucleophilic substitution reaction between a metal salt of an unsaturated carboxylic acid and a haloorganoalkoxysilane to form an acryloyloxysilane.

Examples of the catalysts includes, but are not limited to, phase-transfer catalyst that are amines, such as triethylamine, dimethylaniline, 1,8-diazabicyclo[5.4.0]undec-7-ene, 1,4-diazabicyclo[2.2.2]octane, and 1,5-diazabicyclo[4.3.0]-non-5-ene; quaternary ammonium compounds, such as tributylmethyl ammonium chloride, triethylcetyl ammonium bromide, didodecyl dimethyl ammonium chloride, distearyl dimethyl ammonium chloride, tricaprylmethyl ammonium chloride, ALIQUAT® 336 [tris(n-$C_8$- and $C_{10}$-alkyl)methyl ammonium chloride], trioctyl methyl ammonium chloride, tetrabutyl ammonium chloride or bromide, tetrapropylammonium bromide, tetrabutylammonium bromide, tetrabutylammonium chloride, tetrapentylammonium bromide, tetrahexylammonium bromide, tetraoctylammonium bromide, methyltributylammonium bromide, and methyltributylammonium chloride; and quaternary phosphonium compounds, such as tetra-n-butylphosphonium bromide, tetra-n-butylphosphonium chloride, methyltri-n-butylphosphonium chloride, methyltri-n-butylphosphonium bromide, n-butyltriphenylphosphonium bromide, n-butyltriphenylphosphonium bromide, n-butyltriphenylphosphonium chloride, methyltriphenylphosphonium chloride and methyltriphenylphosphonium bromide. In one embodiment, the phase-transfer catalyst is tetrabutyl ammonium chloride or bromide, methyltriphenylphosphonium chloride, n-butyltriphenylphosphonium bromide, or tetra-n-butylphosphonium bromide. In one embodiment, combinations of catalysts are used.

The catalyst, such as phase-transfer catalysts, are made by processes known in the art. Many of these compounds are available commercially.

The process of making the acryloyloxysilane may comprise a co-catalyst; alternatively the process of the invention further comprises a co-catalyst, wherein the co-catalyst is metal salt, alternatively a metal salt with iodide, alternatively potassium iodide.

The process of making the acryloyloxysilane may, optionally, be carried out in the presence of one or more free-radical inhibitors. As used herein, "inhibitors" are compounds that inhibit free-radical polymerization reactions.

Examples of inhibitors include, but are not limited to, amines, such as ethylenediaminetetraacetic acid, aromatic amines, such as N,N'-p-phenylenediamine, N,N'-di-O-naphthyl-p-phenylenediamine, and phenothiazine, quinines, hydroquinones, such as hydroquinone monomethyl ether, sterically hindered phenols, such as 2,6-di-tertbutylphenol, 2,6-di-tert-butyl-4-methylphenol, 2,6-di-tert-butyl-4-(N,N-dimethylamino)methylphenol, and butylated hydroxytoluene, and stable free radicals.

The inhibitors are made by processes known in the art. Many of these inhibitors are available commercially.

The reacting to form the acryloyloxysilane may also optionally be conducted in the presence of a non-polar solvent, alternatively the reacting is in the presence of a non-polar solvent.

The reactor for carrying out the reacting to form the acryloyloxysilane can be any suitable reactor for reacting a metal salt of an unsaturated carboxylic acid with a haloorganoalkoxysilane in the presences of a phase-transfer catalyst. For example, a glass, round-bottom flask may be used.

In one embodiment, the reactants used to form the acryloyloxysilane are added to the reactor in any order. Alternatively, the metal salt of the unsaturated carboxylic acid, catalyst, a portion of the haloorganoalkoxysilane, and, if present, alcohol, water, co-catalyst, inhibitors and non-polar solvent, are added to the reactor and heated; after heating, the remaining amount of haloorganoalkoxysilane is added to the reactor. Alternatively, 100% of each of the metal salt of the unsaturated carboxylic acid, catalyst, and, if present, alcohol, water, inhibitors and non-polar solvent, and a portion of the haloorganoalkoxysilane are added to the reactor and heated; after heating, the remaining amount of haloorganoalkoxysilane is added to the reactor. As used herein, "a portion" as used in reference to the haloorganoalkoxysilane means up to 75%, alternatively up to 50%, alternatively from 30% to 55% of the total molar amount of the haloorganoalkoxysilane to be added in the process. As used herein, "the remaining amount" as used in reference to the haloorganoalkoxysilane added in the process of the invention means the amount of haloorganoalkoxysilane remaining to be added to the process after subtracting the portion of haloorganoalkoxysilane already added to the reactor from the total molar amount of haloorganoalkoxysilane to be added to the process, alternatively up to 75%, alternatively up to 45%, alternatively up to 25%, based on the total molar amount of haloorganoalkoxysilane to be added to the process, of the haloorganoalkoxysilane.

The rate of addition of the reactants in the process to form the acryloyloxysilane may controlled. The haloorganoalkoxysilane may be gradually introduced to the reactor and to the metal salt of the unsaturated carboxylic acid to prevent unwanted exotherms and improve processing.

The reaction to form the acryloyloxysilane is typically carried out at a temperature of from 50 to 160° C., alternatively from 80 to 140° C., alternatively from 80 to 130° C., alternatively from 80 to 100° C., alternatively from 85 to 95° C., and at a pressure from 0 to 1000 kPag, alternatively from 50 to 200 kPag, alternatively from 80 to 150 kPag, alternatively at atmospheric pressure. The reactants are typically combined as described above at ambient temperature and then the combination brought to the temperatures and pressures described above.

The reaction to produce the acryloyloxysilane is typically carried out until at least 50% (w/w) of the haloorganoalkoxysilane has reacted, alternatively until at least 80% of the haloorganoalkoxysilane has reacted, alternatively until from 90 to 100% of the haloorganoalkoxysilane has reacted. The progression of the reaction of the haloorganoalkoxysilane can be monitored by standard processes known in the art, for example by gas chromatography (GC).

Typically, the time required to carry out the reaction to produce the acryloyloxysilane is at least 30 minutes, alternatively from 60 to 6000 minutes, alternatively from 120 to 1000 minutes, alternatively from 600 to 720 minutes.

The molar ratio of the metal salt of the unsaturated carboxylic acid to the haloorganoalkoxysilane in the reaction to form the acryloyloxysilane is typically from 0.5-1.5:1, alternatively from 0.9-1.1:1, alternatively from 1-1.05:1.

The phase-transfer catalyst may be used in a catalytic effective amount in the reaction to form the acryloyloxysilane. As used herein, a "catalytic effective amount" is an amount that will catalyze the nucleophilic substitution reaction between the haloorganoalkoxysilane and the salt of an unsaturated carboxylic acid to produce an acryloyloxysilane. For example, a catalytic effective amount is at least 0.001% (w/w), alternatively from 0.005 to 0.5%, alternatively from 0.01 to 0.05% (w/w), based on the combined weight of the phase-transfer catalysts, the haloorganoalkoxysilane, the salt of an unsaturated carboxylic acid, and the mineral spirits.

In one embodiment the reacting to form the acryloyloxysilane is in the presence of water, alternatively in the presence of at least 100 ppmw, alternatively at least 2000 ppw, alternatively from 100 to 2400 ppmw, alternatively from 3500 to 5000 ppmw, based on the weight of all materials in the reaction, of water. The amount of water in the reaction is produced by processes known in the art, considering the amount of water contributed by all the materials in the reaction with the balance desired produced by adding additional water if the amount for the other ingredients is less than the desired amount, or by removing water from one or more of the materials in the reaction by methods known in the art if the amount of water is more than desired.

In one embodiment, the reacting to form the acryloyloxysilane is conducted in the presence of the alcohol described above, alternatively at least 80 ppmw, alternatively from 80 to 6400 ppmw, alternatively from 80 to 4800 ppmw, based on the weight of alcohol and all other materials in the reaction, of the alcohol described above. The amount of alcohol in the reaction is produced by processes known in the art, considering the amount of alcohol contributed by all the materials in the reaction with the balance desired produced by adding additional alcohol if the amount for the other ingredients is less than the desired amount, or by removing alcohol from one or more of the materials in the reaction by methods known in the art if the amount of alcohol is more than desired.

In one embodiment, the reacting to form the acryloyloxysilane is conducted in the presence of water and the alcohol described above, alternatively in the presence of from 100 to 5000 ppmw water and from 80 to 6400 ppmw alcohol, alternatively from 100 to 1200 ppmw of water and from 80 to 4800 ppmw alcohol, alternatively from 1000 ppm water to 4800 ppmw of water, and from 80 to 1000 ppmw of alcohol, alternatively from 400 to 800 ppmw of water, and from 4500 to 5000 ppmw alcohol, alternatively from 2100 to 3500 ppmw of water, and from 3100 to 3500 ppmw methanol, where ppmw is calculated based on the weight of all materials in the reaction. The amount of water and alcohol present is achieved in the same way as described above for the individual materials.

When included, the inhibitor in the reaction to form the acryloyloxysilane is typically from 1 to 10,000 ppmw, alternatively from 10 to 2500 ppmw, alternatively from 1800 to 2400 ppmw, based on the combined weight of the inhibitor, the haloorganoalkoxysilane, the metal salt of the unsaturated carboxylic acid, and the alcohol.

The non-polar solvent is present in the reaction to form the acryloyloxysilane at a sufficient amount to increase the removal of the haloorganoalkoxysilane, alternatively from 10 to 90% (w/w), alternatively 15 to 80% (w/w), alternatively from 25 to 60% (w/w), based upon the combined weight of the non-polar solvent, the acryloyloxysilane, and the metal halide.

The co-catalyst in the reaction to form the acryloyloxysilane is present in a catalytic effective amount. A catalytic effective amount as used herein with respect to the co-catalyst is an amount sufficient to act as a co-catalyst in the reaction of the metal salt of the carboxylic acid and the haloorganoalkoxysilane, alternatively a catalytic effective amount is in a ratio to the catalyst from 0.01 to 10 (catalyst/co-catalysts), alternatively from 0.1 to 5, alternatively from 0.25 to 2, alternatively from 0.4 to 1.1.

The reaction to form the acryloyloxysilane is typically carried out in an inert gas atmosphere; however, it may be carried out in air. The inert gas is a gas that is unreactive toward the components present in the reaction mixture under reaction conditions. Examples of inert gases are nitrogen and argon.

The reaction to form the acryloyloxysilane forms a mixture comprising an acryloyloxysilane, and a metal halide having the formula $M^{a+}X^{-}_{a}$ (III), wherein $X^{-}$ is a halide anion. As used herein, "acryloyloxysilane" is intended to include materials that may not necessarily be named an acryloyloxysilane according to the formula, but includes the acryloyloxy functionality. For example, it is contemplated that acryloyloxy may include sorbyloxy functional groups.

The metal halide is according to the formula $M^{a+}X^{-}_{a}$ (III), wherein M and a are as defined and exemplified above for the metal salt of the unsaturated carboxylic acid, and $X^{-}$ is a halide anion. Examples of halide anions include chloride, bromide, fluoride and iodide. Examples of the metal halide include, but are not limited to sodium chloride, sodium bromide, sodium iodide, potassium chloride, potassium bromide, potassium iodide, magnesium chloride, magnesium bromide, magnesium iodide, calcium chloride, calcium bromide, and calcium iodide.

The process of the invention may also comprise removing at least a portion of the metal halide from the mixture comprising an acryloyloxysilane and a metal halide. As used herein, "a portion" means enough to reduce the metal halide in the acryloyloxysilane to within the ranges described below. For example, a portion is typically at least 50%, alternatively at least 90%, alternatively at least 99.99%, of the initial amount of the metal halide in the mixture.

The metal halide may be removed from the mixture comprising an acryloyloxysilane and a metal halide by processes known in the art for removing a solid metal halide from an organic material. The metal halide may be removed by, for example, filtration, decantation, washing, or a combination of filtration, decantation and washing. In one embodiment, the metal halide is removed by filtration or decantation. In another embodiment, the metal halide is removed by decanting the acryloyloxysilane from the metal halide followed by washing the metal halide with a brine solution.

After the step of removing at least a portion of the metal halide from the mixture comprising an acryloyloxysilane and a metal halide, the acryloyloxysilane typically has less than 10,000 parts per million by weight (ppmw), alternatively from 1 to 1000 ppmw, alternatively from 10 to 100 ppmw, based on the weight of the acryloyloxysilane, of the metal halide.

The haloorganoalkoxysilane in the mixture of a acryloyloxysilane, a haloorganoalkoxysilane and a non-polar solvent is as described above in the process for producing the acryloyloxysilane.

The non-polar solvent in the mixture of a acryloyloxysilane, a haloorganoalkoxysilane and a non-polar solvent has a dielectric constant below 10, alternatively below 5, alternatively from 1 to 5.

In one embodiment, the non-polar solvent comprises a branched-chain alkane, alternatively a branched-chain alkane and a straight-chain alkane, alternatively two or more branched-chain alkanes and a straight-chain alkane. The branched-chain alkane has from 5 to 20, alternatively from 6 to 16, alternatively 6 to 13 carbon atoms. In one embodiment, the branched-chain alkane comprises a mixture of branched chain alkanes, alternatively a mixture of branched chain alkanes where 25 to 35% (w/w) of the mixture of branched-alkanes have from 10 to 13 carbon atoms and 65 to 75% (w/w) of the mixture of branched-chain alkanes have from 9 to 11 carbon atoms.

The straight-chain alkane has from 5 to 14 carbon atoms, alternatively from 6 to 14, alternatively 6 to 13, alternatively from 6 to 10, alternatively 7 carbon atoms. The straight-chain alkane may be a mixture of straight-chained alkanes.

In one embodiment, the non-polar solvent comprises less than 5% (w/w), alternatively less than 1% (w/w), alternatively less than 0.5% (w/w), alternatively less than 500 ppm (by weight) of aromatic hydrocarbon, based on the weight of all hydrocarbons in the non-polar solvent.

The non-polar solvent comprises from 0 to 99.5% (w/w), alternatively from 80 to 99% (w/w), alternatively from 90 to 99% (w/w), alternatively from 90 to 98% (w/w), based on the total amount of non-polar solvent, of the straight-chain alkane, alternatively, n-heptane.

The non-polar solvent further comprises 0.5 to 100% (w/w), alternatively 1 to 20% (w/w) alternatively 1 to 10% (w/w), alternatively 1 to 8% (w/w), alternatively 3 to 8% (w/w), based on the total amount of non-polar solvent, of the branched-chain alkane.

In one embodiment, the branched-chain alkane and straight-chain alkane have a boiling point from 50 to 250° C., alternatively 50 to 220° C., alternatively from 60 to 240° C., alternatively from 65 to 230° C.

The non-polar solvent has a density less than 1.0 grams per milliliter (g/mL), alternatively from 0.6 to 0.9 grams per mL, alternatively from 0.65 to 0.75 g/mL, at 25° C.

Examples of the straight-chain alkane include, but are not limited to, n-pentane, n-hexane, n-heptane, n-octane, n-nonane, n-decane, n-undecane, n-dodecane, and n-pentadecane. Examples of the branched-chain alkane include, but are not limited to, branched-alkanes having 6 to 16 carbon atoms, alternatively 6 to 13 carbon atoms, alternatively 9 to 13 carbon atoms, alternatively isoalkanes and mixtures thereof such as those sold under the ISOPAR® trademark such as ISOPAR G FLUID. In some embodiments, the non-polar solvent may contain additional components including, but not limited to, cyclopentane, cyclohexane, cyclooctane, cyclohexane, cis-cyclooctene, tert-butyl methyl ether and di-n-butyl ether.

In one embodiment, the non-polar solvent is a mixture of alkanes comprising 6 to 13 carbon atoms and a boiling point from 65 to 230° C. (such as those sold under the trade name ISOPAR® G FLUID), alternatively heptane, alternatively a mixture of straight-chain alkanes and branched-chain alkanes comprising 6 to 13 carbon atoms and a boiling point from 65 to 230° C. (such as those sold under the trade name ISOPAR® G FLUID).

The mixture of an acryloyloxysilane, a haloorganoalkoxysilane and a non-polar solvent may be made in the process of making the acryloyloxysilane, where the haloorganoalkoxysilane is unreacted starting material, and the non-polar solvent, or a component thereof, is solvent included in such process of making the acryloyloxysilane. In this case, the mixture of an acryloyloxysilane, a haloorganoalkoxysilane and a non-polar solvent may be the crude reaction product mixture after the reaction to form the acryloyloxysilane is completed and/or after subsequent purification steps, like filtration, washing, or distillation or a combination thereof. Alternatively, the mixture may be prepared by adding the non-polar solvent to the acryloyloxysilane and haloorganoalkoxysilane after the reaction to form the acryloyloxysilane but prior to or after any purification steps, alternatively the mixture may be prepared by adding the non-polar solvent to a mixture of the acryloyloxysilane and the haloorganoalkoxysilane after the mixture of the acryloyloxysilane and the haloorganoalkoxysilane has undergone an initial purification process such distillation, washing, and/or filtration, alternatively the mixture is prepared by adding the non-polar solvent to a mixture of the acryloyloxysilane and the haloorganoalkoxysilane after the mixture of the acryloyloxysilane and the haloorganoalkoxysilane has undergone an initial purification process such vaporization of an impurity such as solvent. When the non-polar solvent is added after the process to produce the acryloyloxysilane, solvents used in the process may or may not be removed prior to the formation of the mixture of an acryloyloxysilane, a haloorganoalkoxysilane and a non-polar solvent.

The mixture of an acryloyloxysilane, a haloorganoalkoxysilane and a non-polar solvent comprises from 0 to 5% (w/w), alternatively 0 to 1% (w/w), alternatively 0 to 0.1% (w/w), alternatively from 0.01 to 5% (w/w), alternatively from 0.01 to 1% (w/w), alternatively from 0.01 to 0.1% (w/w), based on the weight of the mixture, of haloorganoalkoxysilane.

The mixture of an acryloyloxysilane, a haloorganoalkoxysilane and a non-polar solvent comprises from 60 to 100% (w/w), alternatively 85 to 100% (w/w), alternatively 97 to 100% (w/w), alternatively 60 to 99.5% (w/w), alternatively 85 to 99.5% (w/w), alternatively 97 to 99.5% (w/w), based on the weight of the mixture, of the acryloyloxysilane.

The mixture of an acryloyloxysilane, a haloorganoalkoxysilane and a non-polar solvent comprises from 0.05 to 40% (w/w), alternatively 0.05 to 30% (w/w), alternatively 0.05 to 5% (w/w), alternatively 0.05 to 0.5% (w/w), alternatively 1 to 8% (w/w), based on the weight of the mixture, of the non-polar solvent.

In one embodiment, the mixture of an acryloyloxysilane, a haloorganoalkoxysilane and a non-polar solvent may comprise up to 20% (w/w) alternatively, up to 10% (w/w), alternatively up to 5%, alternatively up to 0.5, alternatively from 0.01 to 0.5, of other materials such as low boiling materials such as methanol, ethanol, or propanol or high boiling materials such as dimers or other oligomers of the acryloyloxysilane.

The process is conducted in equipment for vaporizing and separating one component from the other components of a mixture. One skilled in the art would be able to select appropriate equipment and understand how the equipment should be used. For example, the process may be conducted in a distillation apparatus, a short path distillation unit, a wiped film evaporator (WFE)/thin film evaporator (TFE), or a falling film evaporator (FFE). These types of equipment are known in the art. These evaporators may be used in series together with the same type of evaporator or with different evaporator types. For example, a falling film evaporator may be used in series with a WFE.

As used herein, a short path distillation unit refers to equipment that uses a thermal separation technique that employs an internal condenser and wiper blades to form a thin film of material on a heated surface. The WFE/TFE are similar to the short path distillation unit except that it does not necessarily employ an internal condenser. While the WFE also uses a rotor blade to form a thin film to maximize surface area and minimize thermal contact time, many WFE's utilize an external condenser. The falling film evaporator typically also involves a thin film and a heated surface, where the heated surface is a vertical cylinder, although the geometry may vary, but falling film evaporators do not use a blade or wiper to form the film. Vacuum equipment is also typically incorporated in the evaporator equipment.

The mixture of an acryloyloxysilane, a haloorganoalkoxysilane and a non-polar solvent is subjected to temperature conditions by applying heat to the mixture. The temperature is sufficient, at the pressure conditions, to vaporize a portion of the non-polar solvent, the haloorganoalkoxysilane, or the non-polar solvent and the haloorganoalkoxysilane from the mixture, alternatively from 50 to 230° C., alternatively from 90 to 210° C., alternatively from 130 to 190° C. One skilled in the art would know how to heat the mixture in equipment designed for such separations as described above. The heat could be provided by an electrical element or potentially steam or other heat transfer fluid.

The mixture of an acryloyloxysilane, a haloorganoalkoxysilane and a non-polar solvent is subjected to pressure is sufficient, at the temperature conditions, to vaporize a portion of the non-polar solvent, the haloorganoalkoxysilane, or the non-polar solvent and the haloorganoalkoxysilane from the mixture, alternatively the pressure is is from 0 to atmospheric pressure, alternatively from 0 to 102 kPa, alternatively from 0 to 14 kPa, alternatively from 0 to 4 kPa, alternatively from >0 to 102 kPa, alternatively from >0 to 14 kPa, alternatively from >0 to 4 kPa. To achieve pressures below atmospheric pressure, a vacuum pump may be used. One skilled in the art would know how to reduce pressure below atmospheric pressure. The pressures are absolute pressures.

The time for the vaporization is dependent upon the heating, temperature, and pressure conditions, with lower temperatures and pressures requiring more time to vaporize the non-polar solvent, the haloorganoalkoxysilane, or the non-polar solvent and the haloorganoalkoxysilane from the mixture, the amount of material to be vaporized, and the equipment used to conduct the process. The time for the vaporization is sufficient to vaporize the non-polar solvent, the haloorganoalkoxysilane, or the non-polar solvent and the haloorganoalkoxysilane from the mixture, alternatively the time is from 0.01 seconds to 15 hours, alternatively from 5 seconds to 11 hours, alternatively from 1 minute to 6 hours. One skilled in the art would know how to determine the time required for vaporization.

The flow rate of the mixture of an acryloyloxysilane, a haloorganoalkoxysilane and a non-polar solvent through the evaporator will vary depending upon the temperature and pressure conditions, the size of the evaporator, and the number of times the process may be repeated in the same or different evaporators. One skilled in the art would understand how to adjust flow rate, temperature, and pressure to optimize the separation while minimizing negative properties associated with the varying conditions such as the formation of side products. For example, higher temperatures may be possible with higher flow rates, and lower temperatures are possible with lower pressure or higher vacuum. In one embodiment the flow rate is from 10 to 100 kilograms per hour per meter squared (kg/hr·m$^2$), alternatively from 30 to 70 kg/hr·m$^2$, alternatively from 50 to 70 kg/hr·m$^2$.

The purification process may be repeated using the same or different temperature and pressure conditions.

The purification process of the invention can be run in batch, semi-continuous, or continuous processes.

The purified mixture comprising the acryloyloxysilane comprises from 85 to 100% (w/w), alternatively 85 to 98% (w/w), alternatively 97 to 100% (w/w), alternativerly 97 to 98% (w/w), alternatively 97 to 99.5%, based on the weight of all materials in the acryloyloxysilane, of acryloyloxysilane.

The purified mixture comprising the acryloyloxysilane comprises from 0 to 1% (w/w), alternatively from 0 to 0.1% (w/w), alternatively from 0.01 to 0.1% (w/w), based on the weight of all materials in the acryloyloxysilane, of haloorganoalkoxysilane.

The purified mixture comprising the acryloyloxysilane comprises up to 5% (w/w), alternatively up to 0.5% (w/w), alternatively from 1 to 0.5% (w/w), alternatively from 0.01 to 0.5% (w/w), based on the weight of all materials in the acryloyloxysilane, of non-polar solvent.

The process may further comprise subjecting the purified mixture to temperature and pressure conditions sufficient to vaporize the acryloyloxysilane, condensing the vaporized acryloyloxysilane, and collecting the condensed acryloyloxysilane to form a final purified acryloyloxysilane product. One skilled in the art would understand how to determine the temperature and pressure conditions needed to vaporize the acryloyloxysilane. In one embodiment, the temperature and pressure conditions to vaporize the acryloyloxysilane are as described above with respect to the mixture of the acryloyloxysilane, the non-polar solvent, and the haloorganoalkoxysilane.

The equipment used to vaporize the acryloyloxysilane is as described above with respect to subjecting the mixture of the acryloyloxysilane, the non-polar solvent, and the haloorganoalkoxysilane to conditions to vaporize the non-polar solvent and/or the haloorganoalkoxysilane.

The final purified acryloyloxysilane product may comprise from 85 to 100% (w/w), alternatively 85 to 98% (w/w), alternatively 97 to 100% (w/w), alternativerly 97 to 98% (w/w), alternatively 97 to 99.5%, based on the weight of all materials in the acryloyloxysilane, of acryloyloxysilane.

The final purified acryloyloxysilane product may comprise from 0 to 1% (w/w), alternatively from 0 to 0.1% (w/w), alternatively from 0.01 to 0.1% (w/w), based on the weight of all materials in the acryloyloxysilane, of haloorganoalkoxysilane.

The final purified acryloyloxysilane product may comprise up to 5% (w/w), alternativerly up to 0.5% (w/w), alternatively from 1 to 0.5% (w/w), alternatively from 0.01 to 0.5% (w/w), based on the weight of all materials in the acryloyloxysilane, of non-polar solvent.

The processes of the present invention produces purified acryloyloxysilanes. The acryloyloxysilane of the invention may be used as a coupling agent for unsaturated resin or polymer systems, an adhesion promoter at organic-inorganic interfaces, and as a surface modifier.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 1

List of abbreviations used in the examples.

| Abbreviation | Word |
|---|---|
| g | gram |
| Me | methyl |
| wt | weight |
| % | percent |
| mol | mole |
| mmol | millimole |
| hr | hour |
| ° C. | degrees Celsius |
| NA | Not Applicable |
| mL | milliliters |
| solids content | (wt. of dried sample/wt. of initial sample) × 100 and determined as described below |
| rpm | revolutions per minute |
| ppmw | parts per million by weight |
| PTZ | Phenothiazine |
| BHT | butylated hydroxytoluene |
| NaOEt | sodium ethoxylate |
| TBAB | tetrabutylammonium bromide |
| TBA | tributylamine |
| DBU | 1,8-diazabicyclo[5.4.0]undec-7-ene |
| CPTES | γ-chloropropyltriethoxysilane |
| g-ATE | γ-acryloyloxypropyltriethoxysilane |
| PTC | Phase-transfer catalysis |
| EDTA-NA | ethylenediaminetetraacetic acid disodium salt |
| CPTMS | γ-chloropropyltrimethoxysilane |
| g-STM | γ-sorbyloxypropyltrimethoxysilane |
| % organic recovery rate | (isolated organics/theoretical weight of organics) × 100 |
| organics | organoalkoxysilane product and non-polar solvent |
| Isopar G | Isopar G Fluid is produced from petroleum-based raw materials which are treated with hydrogen in the presence of a catalyst to produce a low odor, low aromatic hydrocarbon solvent. The major components are isoalkanes. CAS No: 64742-48-9. Isopar G comprises 30% isoalkanes having from of branched chain alkanes having from 10 to 13 carbon atoms and 70% of the mixture of branched-chain alkanes have from 9 to 11 carbon atoms. |
| Yield | In the case of the distillate comprising the acryloyloxysilane, total mass of purified acryloyloxysilane including impurities divided by the total mass of crude acrylolyoxysilane including impurities from previous pass through evaporator. In the case of the residue comprising the acryloyloxysilane, the total mass of residue after a pass through the evaporator divided by the total mass of the residue from the previous pass (if a previous pass through the evaporator has been made) or the crude acryloyloxysilane feed before making a pass through an evaporator. |
| LB | Low Boilers. Includes any solvent |
| HB | High Boilers. Materials boiling over the boiling point of the acryloyloxysilane. |

Acryloyloxysilane Preparation

A jacketed 5 L baffled reactor equipped with a mechanical agitator, thermometer, and condenser was loaded with 980 g Isopar G, 1000 g potassium sorbate, and 1320 g CPTMS. The stabilizers PTZ (2.4 g), BHT (2.3 g), and EDTA-Na$_4$ (2.3 g), and TBAB (36.5 g) were added sequentially. After allowing the contents of the reactor to mix for 10 min., water was added for some of the examples as shown in Table 1. Methanol was also added in varying amount as indicated in Table 1. This was accomplished by either distilling the CPTMS to reduce methanol from an initial value of 0.84% methanol or by adding additional methanol to the CPTMS. CPTMS with the desired methanol concentration was added to the reactor to achieve the desired overall methanol concentration as shown in Table 1. After heating the reactor to the temperature set point, the temperature was held constant for 5 to 10 hours at atmospheric pressure until the reaction was complete. The time required to complete the reaction varied depending on methanol and water concentration as well as temperature.

The contents of the reaction were then filtered using a pressure filter to remove potassium chloride. The same procedure and equipment, including filtration equipment, was used with all runs in Table 1 except for variation in methanol and water concentration and reaction temperature as shown in Table 1.

TABLE 1

| Run | Water (PPM) | Methanol (PPM) | Reaction Temperature (° C.) | g-STM Yield (%) | Filtration Rate (g/min) |
|---|---|---|---|---|---|
| 1 | 490 | 3300 | 105 | 95 | 49 |
| 2 | 790 | 3300 | 105 | 93 | 66 |
| 3 | 1100 | 3300 | 105 | 90 | 95 |
| 4 | 2100 | 3300 | 105 | 87 | 103 |
| 5 | 3500 | 3300 | 105 | 73 | 103 |
| 6 | 725 | 80 | 105 | 92 | 41 |
| 7 | 725 | 1900 | 105 | 87 | 65 |
| 8 | 725 | 2500 | 105 | 87 | 82 |
| 9 | 725 | 4800 | 105 | 89 | 117 |
| 10 | 725 | 5600 | 105 | 90 | 98 |
| 11 | 725 | 6400 | 105 | 90 | 38 |
| 12 | 725 | 3300 | 85 | 88 | 99 |
| 13 | 725 | 3300 | 95 | 94 | 88 |
| 14 | 725 | 3300 | 105 | 93 | 84 |
| 15 | 725 | 3300 | 115 | 89 | 31 |

General Purification Methodology

A glass 2" short path distillation unit was used. Metal heating panels on the outside of the short path distillation unit column were used to provide heat to the system. A thermocouple and temperature controller were used to control the temperate at the interface of the glass and metal panels on the bottom half of the short path distillation unit. A vacuum pump and vacuum regulator were used to control pressure in the system. A peristaltic pump was used to feed material to the short path distillation unit at a rate of 30 ml/min. Cooling fluid was fed to the internal condenser to maintain temperature at 0° C. The wiper blades were polytetrafluoroethylene (PTFE) and set to a speed of about 1200 RPM. Two to four passes through the system were used to purify the crude acryloyloxysilane.

The crude acryloyloxysilane to be purified was prepared using the general procedure above for acryloyloxysilane preparation. Each pass through the short path distillation unit results in two cuts; a distillate and a residue. The residue flows down the wall of the short path distillation unit without vaporizing and is collected at the bottom. The distillate is vaporized and condensed in the internal condenser and collected in a separate flask. A dry ice cold trap was used to capture any vapor that did not condense on the internal condenser. Where Isopar G was added during the purification process, the weight percent was based on material present except for the Isopar G (i.e., all solvent not Isopar G, the haloorganoalkoxysilane, the acryloyloxysilane and any other materials in the material). The results in the tables show that the first pass removed the majority of the solvent, which made up 30% of the starting material. Additional stripping passes removed residual solvent, CPTMS, and other low boiling materials. Purified product was further separated from high boiling impurities by vaporizing the product, then condensing the product in the same equipment. The distillate and residue were analyzed by GC after each pass was completed. The same methodology and starting materials were used for each experiment except that solvent composition, temperature, and pressure were varied between experiments. The results and parameters are listed in the following Examples.

Example 1

This example compares the effectiveness of single solvent systems to purify acryloyloxysilane using the process outlined above. In this example, FIG. 1 shows that LB is comprised of approximately 100% (w/w) of either Isopar G solvent (first row of boxes) or Heptane solvent (second row of boxes) with minor amounts (up to 0.5% (w/w)) of methanol. The first box on the left represents the starting material composition before the first pass through the short path distillation unit. The second box represents the composition after the first pass through the short path distillation unit, and the third box represents the composition after second pass. The fourth and last box represents the composition of the distillate after the third pass through the short path distillation unit. The conditions listed represent the temperature and pressure during each pass though the short path distillation unit. The yield shown is specific to each individual pass. For the first and second passes, the yield is the weight percent of the feed to the short path distillation unit remaining as residue. For the third pass, the yield is the weight percent of the feed to the short path distillation unit that leaves the short path distillation unit as the distillate.

Example 2

Figure 2:
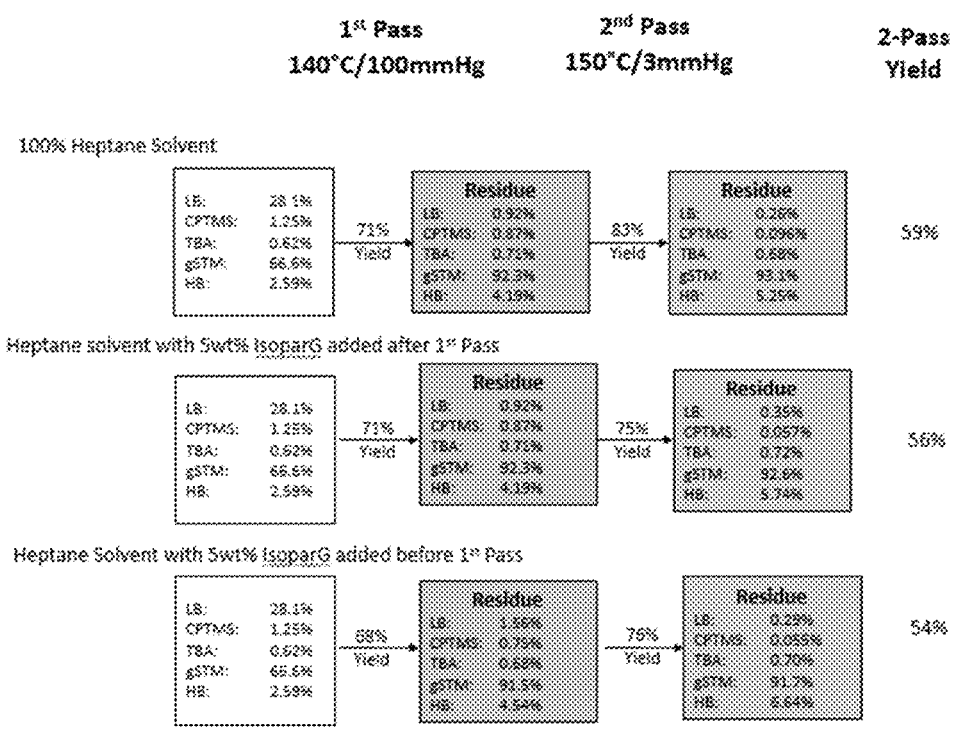
FIG. 2 is a diagram of the process in EXAMPLE 2.

This example compares the effectiveness of adding Isopar G to purify acryloyloxysilane after an initial pass of the crude acryloyloxysilane product to adding Isopar G before an initial pass of the crude acryloyloxysilane product to a 100% heptane solvent system with no Isopar G added. In FIG. 2, the first row of boxes describes 100% (w/w) of heptane solvent (no Isopar G added). The second row of boxes has the results of adding 5% of Isopar G to the residue after an initial purification pass of the starting crude acryloyloxysilane through the short path distillation unit at the conditions listed. The third row of boxes represents the addition of 5% (w/w) Isopar G to the crude acryloyloxysilane before any passes through the short path distillation unit. The acryloyloxysilane is not finally vaporized from the remaining high boiling materials. In the case where Isopar G was added, the GC results shown are before adding the Isopar G. The first and second pass yield shown are specific to each individual pass, which is the weight percent of the feed to the short path distillation unit that remains as residue. The 2-pass yield is the total amount of residue after the second pass divided by the amount of the starting material before first pass, not including the Isopar G added.

Example 3

Figure 3:
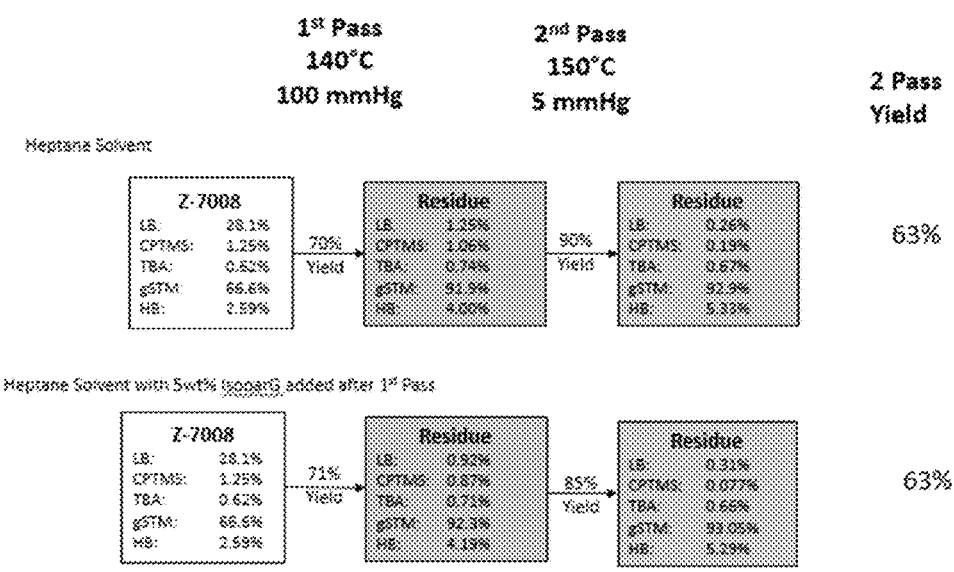
FIG. 3 is a diagram of the process in EXAMPLE 3.

This example compares purification of a 100% (w/w) heptane solvent system to adding Isopar G to a heptane solvent system after the initial pass in the short path distillation unit to purify the crude acryloyloxysilane. In FIG. 3, the first row of boxes are the results for the 100% heptane system. The second row of boxes are the results of the addition of adding 5% (w/w) Isopar G after the first pass of the crude acryloyloxysilane through the short path distillation unit. In the case where Isopar G was added, the GC results shown are before adding the Isopar G. the first and second pass yield shown are specific to each individual pass, which is the weight percent of the feed to the short path distillation unit remaining as the residue. The 2-pass yield is the total amount of residue after the second pass divided by the amount of starting material before the first pass, not including the Isopar G added.

That which is claimed is:

1. A process for purifying an acryloyloxysilane, the process comprising:
subjecting a mixture comprising an acryloyloxysilane, a haloorganoalkoxysilane, and a non-polar solvent, wherein the non-polar solvent comprises a mixture of 0.5 to 15% (w/w) of a branched-chain alkane having from 5 to 20 carbon atoms and 85 to 99.5% (w/w) of a straight-chain alkane having from 5 to 14 carbon atoms, based on the weight of the branched-chain and straight-chain alkane in the non-polar solvent, and wherein the non-polar solvent comprises less than 5% (w/w), based on the weight of the non-polar solvent, of an aromatic compound, to a temperature and pressure sufficient to vaporize a portion of the non-polar solvent, the haloorganoalkoxysilane, or the non-polar solvent and the haloorganoalkoxysilane from the mixture to produce a purified mixture comprising the acryloyloxysilane.

2. The process according to claim 1, wherein the process is repeated one or more times using the purified mixture as the mixture comprising an acryloyloxysilane, a haloorganoalkoxysilane, and a non-polar solvent.

3. The process of claim 2, wherein the purified mixture is conveyed from the outlet of the thin film evaporator, wiped film evaporator, falling film evaporator, or short path distillation unit to the inlet of the same or different thin film evaporator, wiped film evaporator, falling film evaporator, or short path distillation unit to perform the heating of the purified mixture and repeat the process.

4. The process of claim 3, wherein the mixture or the purified mixture are flow through the thin film evaporator, the wiped film evaporator, the falling film evaporator, the short path distillation unit at a flow rate of from 10 to 100 kg/hr·m$^2$.

5. The process of claim 2, wherein the temperature and pressure vary from one process repetition to another.

6. The process of claim 2, wherein the process is conducted using a thin film evaporator, a wiped film evaporator, a falling film evaporator, a short path distillation unit, or a series of thin film evaporators, wiped film evaporators, falling film evaporators, short path distillation units.

7. The process according to claim 1, further comprising subjecting the purified mixture to a temperature and pressure sufficient to vaporize the acryloyloxysilane, condensing the vaporized acryloyloxysilane, and collecting the condensed acryloyloxysilane to form a final purified acryloyloxysilane product.

8. The process of claim 7, wherein the process is conducted using a thin film evaporator, a wiped film evaporator, a falling film evaporator, a short path distillation unit, or a series of thin film evaporators, wiped film evaporators, falling film evaporators, short path distillation units.

9. The process of claim 8, wherein the mixture or the purified mixture are flow through the thin film evaporator, the wiped film evaporator, the falling film evaporator, the short path distillation unit at a flow rate of from 10 to 100 kg/hr·m$^2$.

10. The process of claim 7, wherein the temperature and pressure vary from one process repetition to another.

11. The process of claim 1, where the temperature is from 50° C. to 230° C. and the pressure is from 0 to 102 kPa.

12. The process of claim 1, wherein the the acryloyloxysilane has the formula $CR^6_2=CR^1COOR^3Si(OR^4)_nR^5_{3-n}$ (IV), wherein $R^1$ is H, $R^7COO^-M^{a+}$, or $C_1$-$C_6$ hydrocarbyl, $R^3$ is $C_1$-$C_6$ hydrocarbylene, each $R^4$ is independently $C_1$-$C_{10}$ hydrocarbyl, each $R^5$ is independently $R^1$, each $R^6$ is independently H, $C_1$-$C_6$ hydrocarbyl, or $COOR^3Si(OR^4)_nR^5_{3-n}$, $R^7$ is hydrocarbylene having from 1 to 6 carbon atoms, n is an integer from 1 to 3, $M^{a+}$ is an alkali metal cation or alkaline earth metal cation, a is the cationic charge and has a value of 1 or 2.

13. The process of claim 12, wherein the acryloyloxysilane is γ-acryloyloxypropylmethyldimethoxysilane, γ-acryloyloxypropyltrimethoxysilane, γ-sorbyloxypropylmethyldimethoxysilane, γ-sorbyloxypropyltrimethoxysilane, γ-acryloyloxypropyltriethoxysilane, γ-sorbyloxypropyltriethoxysilane, bis(γ-trimethoxysilylpropyl) fumarate, or bis (γ-triethoxysilylpropyl) fumarate.

14. The process of claim 1, comprising forming the mixture comprising the acryloyloxysilane, the haloorganoalkoxysilane, and the non-polar solvent by i) combining the branched-chain alkane having from 5 to 20 carbon atoms during a reaction to form the acryloyloxysilane, ii) combining the branched-chain alkane having from 5 to 20 carbon atoms with the acryloyloxysilane and the haloorganoalkoxysilane after the reaction to form the acryloyloxysilane, or iii) combining the branched-chain alkane having from 5 to 20 carbon atoms with the acryloyloxysilane and the haloorganoalkoxysilane after the reaction to form the acryloyloxysilane and after subjecting the acryloyloxysilane formed by the reaction to an initial purification process.

15. The process of claim 1, wherein the straight-chain alkane is n-heptane and non-polar solvent comprises a mixture of branched-chain alkanes having from 8 to 14 carbon atoms.

16. The process of claim 1, where the non-polar solvent has a boiling point lower than boiling point of the acryloyloxysilane.

17. The process of claim 1, where the non-polar solvent further comprises an additional component selected from the group consisting of cyclopentane, cyclohexane, cyclooctane, cyclohexane, cis-cyclooctene, tert-butyl methyl ether and di-n-butyl ether.

18. The process of claim 1, wherein the process is conducted using a thin film evaporator, a wiped film evaporator, a falling film evaporator, a short path distillation unit, or a series of thin film evaporators, wiped film evaporators, falling film evaporators, short path distillation units.

19. The process according to claim 1, further comprising subjecting the purified mixture to a temperature and pressure sufficient to vaporize the acryloyloxysilane, condensing the vaporized acryloyloxysilane, and collecting the condensed acryloyloxysilane to form a final purified acryloyloxysilane product.

* * * * *